United States Patent
Ratner

(10) Patent No.: US 6,498,036 B1
(45) Date of Patent: *Dec. 24, 2002

(54) METHODS OF TARGETING A CHROMOSOMAL GENE SEQUENCE IN A EUKARYOTIC CELL

(75) Inventor: David I. Ratner, Amherst, MA (US)

(73) Assignee: Trustees of Amherst College, Amherst, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/774,404

(22) Filed: Jan. 31, 2001

Related U.S. Application Data

(63) Continuation of application No. 09/371,670, filed on Aug. 10, 1999, now Pat. No. 6,204,062.
(60) Provisional application No. 60/095,983, filed on Aug. 10, 1998.

(51) Int. Cl.[7] .................. C12N 15/86; C12N 15/64; C12N 15/66; C12N 15/63; C12N 15/85
(52) U.S. Cl. .................. 435/463; 435/91.41; 435/455; 435/471; 435/468; 800/21
(58) Field of Search .............. 435/463, 91.41, 435/455, 471, 468; 800/21

(56) References Cited

U.S. PATENT DOCUMENTS 6,204,062 B1 * 3/2001 Ratner

OTHER PUBLICATIONS

Horie et al. Gene Targeting B A Bector With Hairpin-–Shaped Oligonucleotide Caps vol. 32, No. 6, Apr. 1994 pp. 1041–1048.*
Chitilian et al. Studies of Transplantation Immunology with Major Histocompatibility Complex Knockout Mice vol. 16 No. 2 Journal of Heart and Lui.*
Chang et al. Modification of DNA ends can decrease end joining relates to homologous recombination in mammalian cells vol. 84, pp. 4959–4963 Jul. 1987.*
Katz et al. Homologous recombinations and the repair of double–strand breaks during cotranformation of dictyostelium discoideum Molecular and Cellular Biology Jul. 1988 p. 2779–2786.*
Mahoney et al. Blocking the ends of transforming DNA enhances gene targeting in dictyostelium Gene 203 1997 33–41.*
Capecchi, Mario R., *Science* (1989), vol. 244, pp. 1288–1292.
Chang, Xiu–Bao, et al., *Proc. Natl. Acad. Sci. USA* (1987), vol. 84, pp. 4959–4963.
Cherbas, Lucy, et al., *Genetics* (1997), vol. 145, pp. 349–358.
Chitilian, Hovig, V., et al., *The Journal of Heart and Lung Transplantation* (1997), vol. 16, pp. 153–159.

Dingermann, T., et al., *Developmental Genetics* (1990), vol. 11, pp. 410–417.
Drfiscoll, D. M., et al., *Molecular and Cellular Biology*(1987), vol. 7, pp. 4482–4489.
Goedecke, W., et al., *Nucleic Acids Research* (1994), vol. 22, pp. 2094–2101.
Hasty, P., et al., *Nature* (1991), vol. 350, pp. 243–246.
Hasty, P., et al., *Molecular and Cellular Biology* (1991), vol. 11, No. 9, pp. 4509–4517.
Horie, Kyoji, et al., *J. Biochem* (1994), vol. 115, pp. 477–485.
Katz, Kenneth J., et al., *Molecular and Cellular Biology* (1998), vol. 8, pp. 2779–2786.
Kim, Hyung S., et al., *Nucleic Acids Research* (1986), vol. 6, pp. 3973–3983.
Knecht, David A., et al., *Molecular and CellularBiology* (1986), vol. 6, pp. 3973–3983.
Mansour, Suzanne L., et al., *Nature* (1988), vol. 336, pp. 348–352.
Manstein, Dietmar J., et al., *The EMBO Journal* (1989), vol. 8, pp. 923–932.
Morrison, Alastair, et al., *Gene 202* (1997), pp. 171–176.
Ratner, David I., et al. *UCLA Sumposia on Molecular and Cellular Biology* (1981), vol. XXIII, pp. 595–605.
Shah–Mahoney, Nalini, et al., *Gene 203* (1997), pp. 33–41.
Sun, T. Julia, et al., *Genes & Development* (1991), vol. 5, pp. 572–582.
Thomas, Kirk R., et al., *Molecular and Cellular Biology* (1992), vol. 12, pp. 2919–2923.
Tzimagiorgis, Georgios, et al. *Nucleic Acids Research* (1996), vol. 24, pp. 3476–3477.
Williams J. G., et al., *The EMBO Journal* (1985), vol. 4, pp. 999–1006.
Zhang, Hongbing, et al., *Molecular and Cellular Biology* (1994), vol. 14, pp. 2404–2410.
Horie et al. "Gene Targeting By A Vector With Hairpin-–Shaped Oligonucleotide Caps" Biochemistry and Molecular Biology International vol. 32, 6:1041–1048 Apr. 1994.

* cited by examiner

*Primary Examiner*—Remy Yucel
*Assistant Examiner*—Konstantina Katcheves
(74) *Attorney, Agent, or Firm*—Bromberg & Sunstein LLP

(57) ABSTRACT

The invention provides in one embodiment a composition which is a linear DNA molecule having a desired replacement sequence, and second and third sequences substantially homologous to non-identical portions of the gene and having proximal and distal ends, the proximal ends flanking the desired replacement sequence and the distal ends having a terminating nucleotide analog at each end of the molecule. Another embodiment of the invention provides methods, by blocking the 3' ends of transforming DNA with 2'3' dideoxynucleotides, to reduce the frequency of end-mediated DNA insertion. These methods introduce only one copy of the selectable gene at the target locus to achieve a precise gene disruption, reducing or eliminating undesirable and multiple insertions that occur both non-homologously and at the targeted locus.

9 Claims, 10 Drawing Sheets

Primers for molecular analysis of gene structure

1. For detection by PCR of the desired DG17 knock-out:
   Neo 9962:   TGG GTT TTA AAA TTT TCA AAT AAA TAA TTA ACC AAC CCA
   CP1-143:    GAT CCT AAT AGA ACC CCC ATT CCT TTT T Neo 9962 is SEQ ID NO:1. CP1-143 is SEQ ID NO: 2.
2. For preparation by PCR of the Replaced probe:
   16684:      CAT CTG GTG GTG AAC AAT TTG TTC CAC CTT CAA CG
   18088:      AAT GAT TTA TCA AGA TGT TTG ATG GTA GAG CGT GC
   (Asymmetric PCR product extended from 16684.)

16684 is SEQ ID NO:3. 18088 is SEQ ID NO: 4.
3. For preparation by PCR of the Neo probe:
   Neo2:       ATG GTC AGA CTA AAC TGG CTG ACG
   Neo3:       TTC CAG ACT TGT TCA ACA GGC CAG
   (Asymmetric PCR product extended from Neo3.)

Neo 2 is SEQ ID NO: 5. Neo 3 is SEQ ID NO: 6.
4. For preparation by PCR of the COOH probe:
   KP310-5:    CAA AAG TTC ATC ATG AGT TTT CTT TGA TTG G
   KP310-4:    GCT CAC AAG GTT GTT CAG TGA AAA TTG AAA GG
   (Asymmetric PCR product extended from KP310-5.)

KP310-5 is SEQ ID NO: 7. KP310-4 is SEQ ID NO: 8.
5. For preparation by PCR of the CP1 probe:
   CP1-1:      CAT GAA GAA TAT TTG GAA AGA TTT G
   CP1-2:      CAA GAT AAT CAG CAA CTG GAA GG
   (Asymmetric PCR product extended from CP1-1.)

CP1-1 is SEQ ID NO: 9. CP1-2 is SEQ ID NO: 10.

Figure 5

METHODS OF TARGETING A CHROMOSOMAL GENE SEQUENCE IN A EUKARYOTIC CELL

RELATED APPLICATIONS

This application is a continuation of patent application Ser. No. 09/371,670, filed on Aug. 10, 1999, now U.S. Pat. No. 6,204,062, which in turn claims priority from provisional application Ser. No. 60/095,983, filed Aug. 10, 1998, both of which are hereby incorporated by reference herein.

GOVERNMENT FUNDING

This invention was made in part with government support under grant NSF DCB-8911049 awarded by the National Science Foundation. The government has certain rights in the invention.

FIELD OF INVENTION

The present invention relates to targeting of genes, and more particularly to targeting of chromosomal gene sequences in eukaryotic cells.

BACKGROUND

Gene targeting by means of homologous DNA recombination is a powerful technique for elucidating the function of eukaryotic genes. Depending upon the precise structure and mode of presentation of the added DNA, targeting can result in complete inactivation of the chromosomal target gene or, alternatively, can alter the target's structure or expression in subtle and well-defined ways (Capecchi, M. R. (1989) *Science* 244, 1288–1292). A key distinction in gene targeting is whether the vector and approach used are intended to cause gene replacement or gene insertion (Hasty, P. et al. (1991) Mol. Cell. Biol. 11, 4509–4517). In the first case, two homologous recombination events replace the region under study with a selectable gene (FIG. 1B). In gene insertion, a single recombination event adds the entire foreign DNA molecule to the targeted locus (FIG. 1C). Gene insertion may be accomplished using either a circular plasmid or one which contains a double strand break within the region of homology, and gene replacement utilizes molecules linearized at a point outside of the homologous regions.

Despite the distinctions drawn between mechanisms of gene replacement and insertion, experiments intended to produce gene replacement often result instead, in a variable variable proportion of cases, in gene insertion (Hasty, P. et al. (1991) Mol. Cell. Biol. 11, 4509–4517; Thomas, K. R. et al. (1992) Mol. Cell. Biol. 12, 2919–2923; Zhang, H. et al. (1994) Mol. Cell. Biol. 14, 2404–2410). A locus insertionally targeted may, depending upon the vector design, fail to be inactivated; the insertion event is also subject to reversion (Thomas, K. R. et al.(1992) Mol. Cell. Biol. 12, 2919–2923; Hasty, P. et al. (1991) Nature 350, 243–246). Unintended insertional targeting occurs during the transformation of mammalian cells and of the simple eukaryote Dictyostelium discoideum (Manstein, D. J. et al. (1989) EMBO J. 8, 923–932; Sun, T. J. et al. (1991) Genes Dev. 5, 572–582). Events of this type are thought to occur via the joining in vivo of the linearized ends of the plasmid, recreating a circular vector capable of single-crossover insertion at the homologous locus. There is evidence of prolific end-to-end joining activity (i.e., DNA ligation) in a wide variety of eukaryotes. Ligation in vivo occurs whether the ends introduced are "sticky," blunt, or even incompatible (Goedecke, W. et al. (1994) Nucleic Acids Res. 22, 2094–2101; Katz, K. et al. (1990) Ph.D. thesis, University of Massachusetts). It would be desirable to prevent unwanted end-to-end joining of transfecting molecules, and thereby gene insertion, to promote only the desired double cross-over replacement events.

Chang and Wilson (Chang, X.-B. et al. (1987) Proc. Natl. Acad. Sci., USA 84, 4959–4963) observed that 2'3' dideoxy-blocked DNA ends are unable to be ligated in mammalian cells in vivo. There is no information concerning effects of this biochemical procedure on chromosomal integration or gene targeting.

SUMMARY

An embodiment of the invention is a composition of matter for replacing a target sequence in a gene sequence in a eukaryotic cell, comprising: a linear DNA molecule having (i) a desired replacement sequence, and (ii) second and third sequence substantially homologous to non-identical portions of the gene and having proximal and distal ends, the proximal ends flanking the desired replacement sequence; and a terminating nucleotide analog at each end of the DNA molecule. According to this embodiment, the DNA molecule can comprise in addition (iii) a fourth sequence that confers a lethal phenotype and is located at a site selected from the group consisting of the distal ends of each of the second and third sequences, for example, the fourth sequence is a deleterious tRNA gene.

The invention in another embodiment provides also a method of replacing a target sequence in a gene sequence of a eukaryotic cell, comprising: providing a linear DNA molecule having (i) a desired replacement sequence, and (ii) second and third sequences substantially homologous to non-identical portions of the gene and having proximal and distal ends, the proximal ends flanking the desired replacement sequence; adding a terminating nucleotide analog to each end of the DNA molecule; presenting the resulting DNA molecule to the eukaryotic cell such that the resulting DNA molecule enters arid transforms the cell; and growing the cell to obtain recombinant progeny cells having the desired replacement sequence inserted into the targeted gene.

In a further embodiment of this method, adding the terminating nucleotide analog to the DNA includes adding a 2',3'-dideoxynucleotide, for example, adding the 2',3'-dideoxynucleotide includes using a DNA polymerase. In an alternative embodiment, adding the 2',3'-dideoxynucleotide includes using terminal deoxynucleotidyl transferase.

According to an embodiment of the method, providing the linear DNA molecule includes digesting a plasmid with a restriction enzyme.

According to another embodiment of the method, the desired sequence confers a selectable phenotype.

According to an embodiment of the method, in providing the DNA molecule, such molecule includes (iii) a fourth sequence that confers a lethal phenotype and is located outside of the sites selected from the group consisting of distal ends of the second and third sequences.

According to an embodiment of the method of providing the DNA molecule with the desired sequence that confers a selectable phenotype, the DNA molecule includes (iii) a fourth sequence that confers a lethal phenotype and is located outside of the sites selected from the group consisting of the distal ends of the second and third sequences.

In another embodiment of the invention, a method is provided in which the targeted replacement of a genomic sequence inactivates a function of the gene. The gene can be in the cell of an animal, and the inactivated function of the gene in a cell of an animal produces an animal model for a human disease. In this embodiment, the human disease can be selected from the group consisting of cystic fibrosis, Lesch-Nyhan syndrome, emphysema, and muscular dystrophy.

In another aspect of this method, the inactivated function of the gene in a cell of an animal eliminates production of an antigen by the animal. In this aspect, the inactivated function of the gene in a cell of an animal produces the antigen causes immune rejection of a tissue or organ donated by the animal.

Another embodiment provided by the invention is a method wherein the gene is in the cell of a plant. According to this embodiment, the inactivated function of the gene in a cell of a plant results in elimination of production of an antigen by the plant, for example, where the antigen in the cell of the plant is a human allergen. In this embodiment, the plant can be a peanut plant, *Arachis hypogaea*. Further, the plant can a Brazil nut plant, *Bertholletia excelsa*.

In another aspect of the embodiment provided by this method, the gene is found in the chloroplast DNA in a cell of a plant.

An embodiment of the invention provides a method for correcting a mutation in the gene sequence, for example, a deleterious mutation in the gene sequence, wherein the desired sequence includes a normal allele to a deleterious mutation. The deleterious mutation can be a recessive mutation, for example, a mutation selected from the group consisting of mutations resulting in the diseases: adenosine deaminase deficiency resulting in SCID (severe combined immuno-deficiency), cystic fibrosis, Duchenne muscular dystrophy, phenylketonuria, sickle cell anemia, α-thalassemia, β-thalassemia, breast cancer, and Crigler-Najjar syndrome.

In another embodiment of the invention, the mutation can be a dominant mutation, for example, a mutation selected from the group consisting of mutations resulting in the diseases: achondroplasia, Marfan syndrome, neurofibromatosis, myotonic dystrophy, and Huntington disease.

Another embodiment of the invention is method for treatment of a linearized gene replacement vector, comprising: providing a kit comprising deoxynucleotidyl transferase and a 2',3' dideoxynucleoside triphosphate; and using the kit components to add a dideoxynucleotide to each end of the linearized gene replacement vector. According to the method of this embodiment, the 2',3' dideoxynucleoside triphosphate is selected from the group consisting of 2',3' dideoxyadenosine triphosphate, 2',3' dideoxythymidine triphosphate, 2',3' dideoxycytidine triphosphate, and 2',3' dideoxyguanosine triphosphate.

BRIEF DESCRIPTION OF THE DRAWINGS

FIG. 5 shows the PCR primers used for analysis of gene structure. Symmetric PCR was programmed for 95° C. for 5 min, then held at 55° C. for addition of enzyme. The subsequent reaction was carried out over thirty cycles consisting of 92° C. for 30 sec, 55° C. for 1 min, and 72° C. for 1 min, in the presence of Mg++at 1.5 to 3.0 mM. Conditions for asymmetric (single primer) PCR were identical, and the reaction was carried out over 40 cycles using one percent of the symmetric PCR product as indicated in the figure.

EXAMPLES

The following materials and methods were used throughout the Examples below. Details of specific embodiments of the invention are provided in Shah-Mahoney, N. et al. (1997) Gene 203, 33–41, which is hereby incorporated herein by reference.

Knock-out Vector Construction

Figure 1A:
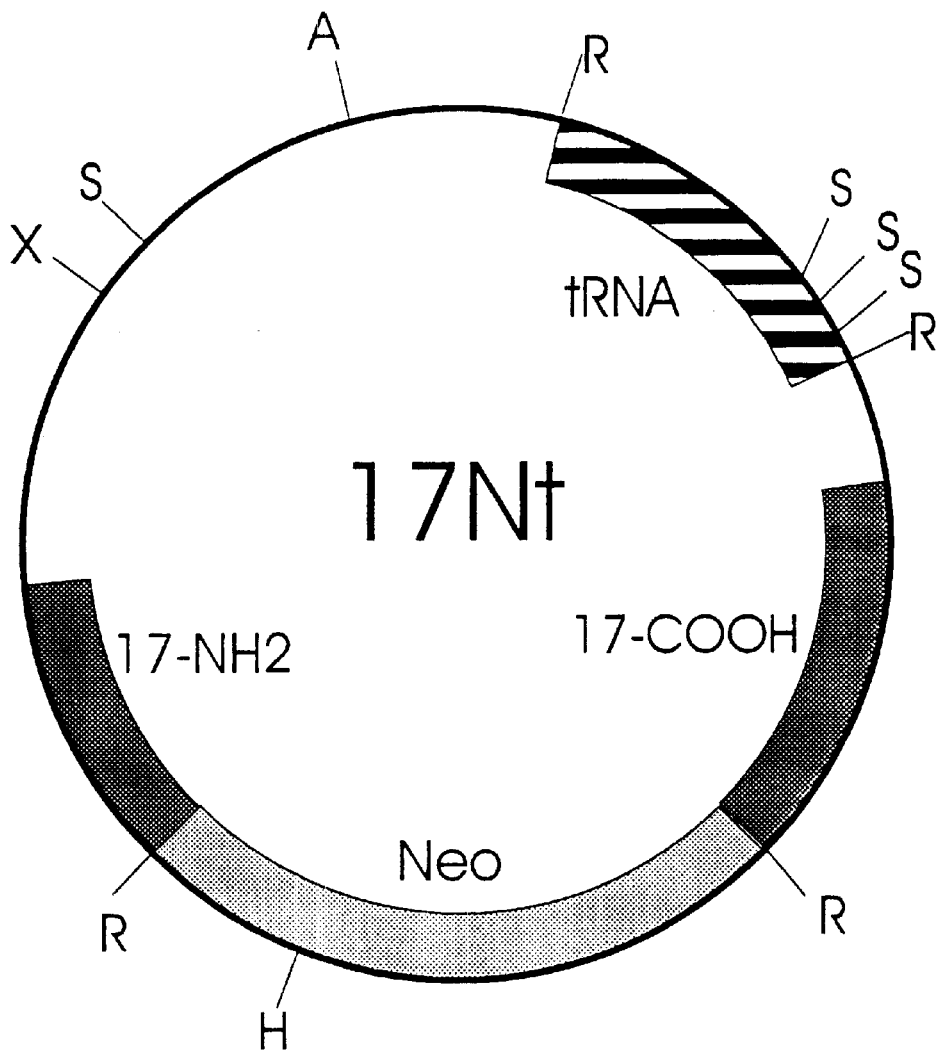
FIG. 1A is a map of plasmid 17Nt used for targeting the DG17 locus of Dictyostelium discoideum. Targeting homology is provided by 5'(17-NH2) and 3'(17-COOH) portions of DG17 DNA, interrupted by the Tn903 neomycin phosphotransferase gene (Neo). The UAA-suppressing glu-tRNA (tRNA) is also indicated, with the remaining backbone derived from pUC18. The plasmid size is 8.0 kb. Sites are shown for key restriction enzymes: A, AlwNI; H, HindIII; R, EcoRI; S, ScaI; X, XmnI.

The internal 0.3 kb EcoRI-EcoRI fragment of gene DG17 was replaced by a selectable neomycin resistance gene (neo) gene in the steps: the 0.9 kb EcoRI-DdeI amino-terminal portion of the gene (Driscoll, D. M. et al. (1987) Mol. Cell. Biol. 7, 4482–4489), cloned into EcoRI-BamHI linearized pUC13, was removed as an EcoRI-HincII fragment. The carboxy-terminal half of the gene, obtained from plasmid DG17 as a 1.4 kb EcoRI-SalI fragment, was cloned into EcoRI-SalI digested pUC19 DNA. The gel-purified amino-terminal fragment was ligated into the carboxy-terminal fragment plasmid which had been digested with NdeI, end-blunted, and then digested with EcoRI. Into the resulting plasmid, opened at its unique EcoRI site, was ligated the 2.1 kb EcoRI-EcoRI neo cassette consisting of the Tn903 neomycin phosphotransferase gene and flanking Dictyostelium actin 15 regulatory sequences (Knecht, D. A. et al. (1986) Mol. Cell. Biol. 6, 3973–3983; Morrison, A. et al. (1997) Gene 202, 171–176). This reconstructs the DG17 gene, but with the internal EcoRI fragment replaced by the neo cassette. Finally, the UAA-suppressing tRNA$^{Glu}$ gene (Dingermann, T. et al. (1990) Dev. Genet. 11, 410–417) was added by transferring the entire DG17-neo fusion from pUC19 as a gel-purified SalI-AatII fragment into SalI-AatII digested, phosphatase-treated pUC18 plasmid into which the tRNA had previously been introduced as a 1.2 kb EcoRI cassette (Morrison, A. et al. (1997) Gene 202, 171–176). The resulting plasmid, 17Nt, is shown in FIG. 1A.

Addition of 2'3' Dideoxy AMP to the Termini of Transforming DNA

Plasmid DNA was digested with AlwNI (4U/$\mu$g, 2 hrs), extracted with phenol, and ethanol precipitated. DNA was end-blocked by treatment for 2 hours at 37° C. in the presence of terminal dideoxynucleotidyl transferase (TdT; Gibco/BRL, 4U/$\mu$g), 2mM $CoCl_2$, and 20 $\mu$M 2'3' dideoxyATP; DNA was again purified by phenol extraction and ethanol precipitation prior to transformation. To test the efficiency of dideoxyAMP addition, a portion of the TdT-treated DNA was incubated with T4 DNA ligase at 200U/$\mu$g at 16° C. overnight and then subjected to gel electrophoresis.

Cell Growth and Transformation

17Nt plasmid DNA was purified from E. coli DH5$\alpha$ using Qiagen resin and digested with XmnI or AlwNI and, where indicated, end-modified using TdT and 2'3' dideoxyATP. Amoebae of strain AX2, grown in HL5 medium to a density of $10^6$/ml, were transformed using the calcium phosphate method (Nellen et al., 1987). DNA was added (12$\mu$g DNA/ $2\times10^7$ cells/dish), cells were incubated for 30 minutes, MES-HL5 medium (pH=7.1) was added and incubation continued for 4 hours, followed by a brief 15% glycerol shock (8 minutes initially, 2 minutes in subsequent experiments). Cells were further incubated overnight in HL5 medium prior to the beginning of selection with 15–20 $\mu$g/ml Geneticin (G418). Foci were picked as they appeared (7–11 days) into multi-well plates, and were sub-cloned by streaking on SM agar/Klebsiella aerogenes plates. Repurified clones were propagated in HL5 containing G418.

Analysis of Transformed Cells

Transformed clones were assessed for targeting using PCR (Kim, H.-S. et al. (1988) Nucleic Acids Res. 16, 8887–8903). An estimated $5\times10^5$ cells were resuspended in 10 mM Tris (pH 8.0) 1mM EDTA solution, incubated at 99° C. for 3 min, and used as template in a PCR reaction using one primer from the neo gene (SEQ ID NO: 1) and a second primer specific for the gene immediately flanking DG17, the CP1 gene encoding cysteine proteinase 1 (SEQ ID NO: 2; see FIG. 5). A positive PCR reaction indicated targeting of the DG17 locus. To distinguish between double and single (5') crossover events, DNA was purified from PCR positive clones by cesium chloride centrifugation (Ratner, D. I. et al. (1981) In, Developmental Biology Using Purified Genes, ICN-UCLA Symposia on Molecular and Cellular Biology, Vol XXIII, D. D. Brown, and C. F. Fox, eds. N. Y.: Academic Press, 595–605), digested with the enzyme indicated (7–15 units/$\mu$g for 2–3 hours), and 3–5 $\mu$g of the digested DNA was loaded per lane of an agarose gel. Following electrophoresis, the gel was then capillary-blotted onto Hybond N+membranes, DNA was UV cross-linked to the membrane, and the blot was hybridized with a succession of probes made either by random priming or by asymmetric PCR (FIG. 5; Ausubel, F. M. et al. (1987) Current Protocols in Molecular Biology. New York: Greene Publishing Associates). Hybridization and washing of the blot were as described previously (Katz, K. S. et al. (1988) Mol. Cell. Biol. 8, 2779–2786). Sizes in kb were determined by comparison with a commercial 1 kb DNA ladder (Gibco/BRL) run on the same gel. For greatest precision, ladder bands were detected on the blot itself by a final hybridization with ladder DNA which had been labelled by successive exonuclease and fill-in reactions of T4 DNA polymerase (Ausubel, F. M. et al. (1987) Current Protocols in Molecular Biology. New York: Greene Publishing Associates).

Example 1

Gene Disruption Vector and Approach

Plasmid DG17-Neo-tRNA (abbreviated 17Nt; FIG. 1A) was used to target gene DG17 (Driscoll, D. M. et al. (1987) Mol. Cell. Biol. 7, 4482–4489) of Dictyostelium. The DG17 gene encodes a putative zinc finger protein. The presence in the Dictyostelium gencome of a closely related gene (FIG. 4) complicates elucidation of DG17 function through gene disruption. To enable the selection of transformed clones, an internal EcoR1 fragment of the DG17 coding region was replaced with a cassette consisting of the Tn903 neomycin phosphotransferase gene ("Neo," conferring resistance to G418) flanked by Dictyostelium actin regulatory signals (Knecht, D. A. et al. (1986) Mol. Cell. Biol. 6, 3973–3983). Regions of homology for gene targeting consisted of 1.1 kb of carboxy-terminal DNA ("17-COOH") and 0.9 kb of amino-terminal and 5' flanking DNA ("17-NH2") extending half-way through the divergent promoter region shared by DG17 and the neighboring gene, CP1 (Driscoll, D. M. et al. (1987) Mol. Cell. Biol. 7, 4482–4489). For counter-selection against non-targeted integration events, which generally involve insertion of the entire plasmid (Mansour, S. L. et al. (1988) Nature 336, 348–352), a lethal Dictyostelium UAA-suppressing tRNA$^{Glu}$ gene ("tRNA") was incorporated into the construct (Morrison, A. et al. (1997) Gene 202, 171–176).

Figure 1B:
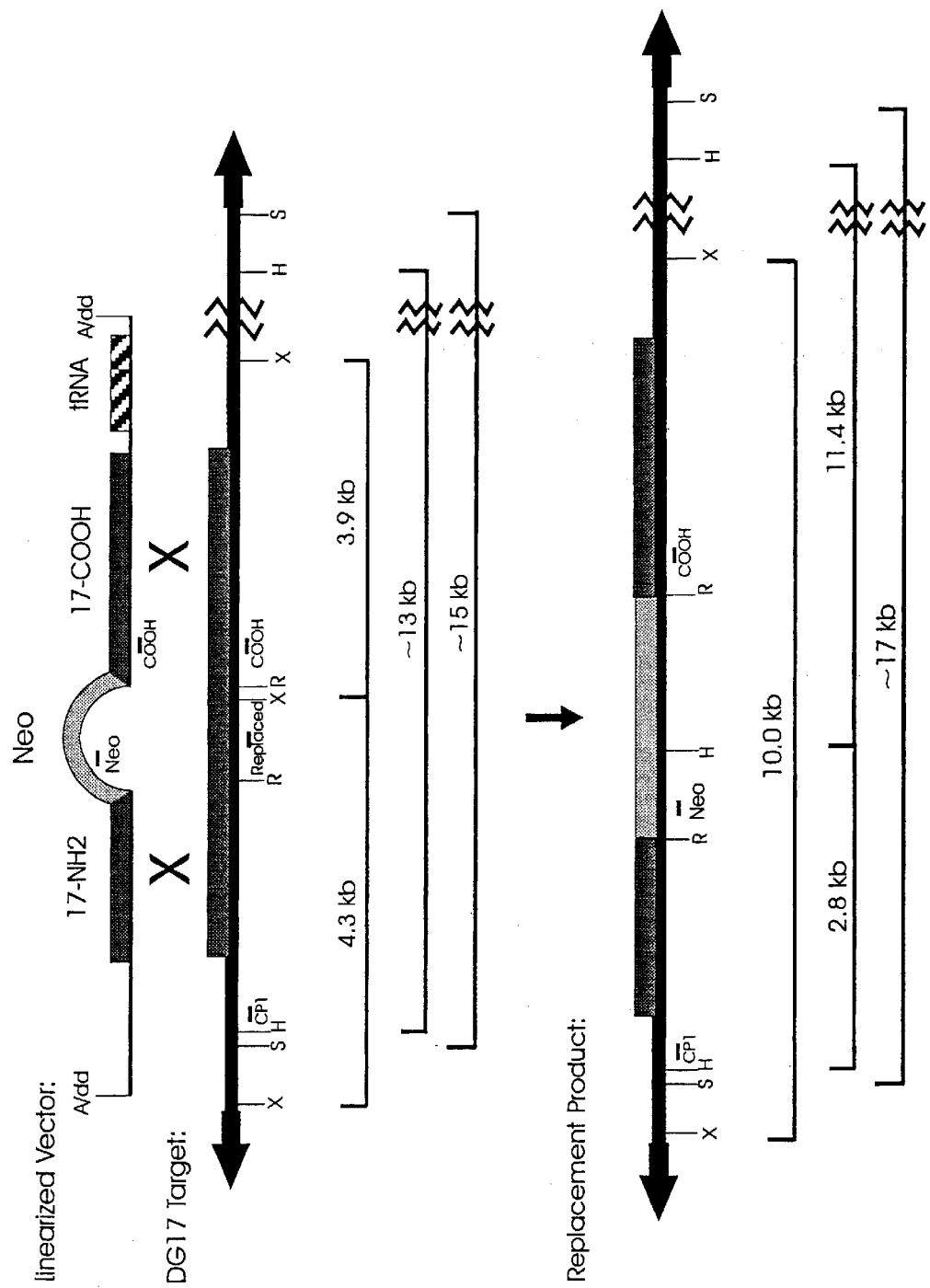
FIG. 1B shows the predicted product of DG17-targeted, double-crossover recombination. 17Nt transforming DNA is shown linearized at the AlwNI site, with its ends blocked by the addition of 2'3' dideoxy-AMP (A/dd). The positions of four hybridization probes are indicated, as are the sizes of diagnostic restriction fragments of the parental and targeted loci.
Figure 1C:
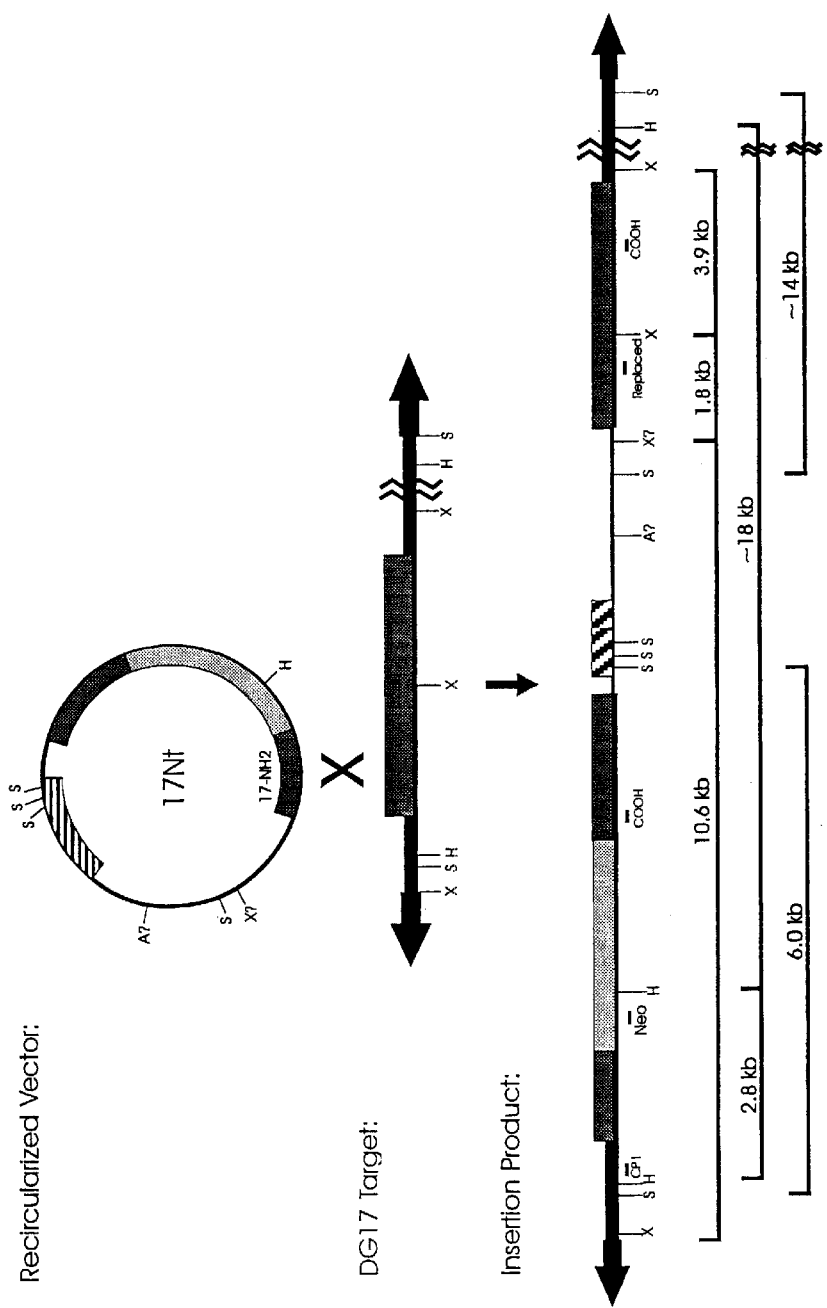
FIG. 1C shows the predicted products of single-crossover recombination between recircularized targeting vector and the DG17 locus. The event depicted is mediated by 5' homology (within the region 17-NH2), and analogous recombination using 3' homology (within 17-COOH) is another possible event. The XmnI and AlwNI sites in the vector are shown as X? and A? to indicate that a site used to linearize the transforming DNA may be restored as a result of in vivo recircularization.

FIG. 1B shows diagnostic restriction fragments predicted for successful targeting of the endogenous gene by double cross-over gene replacement by the linearized 17Nt plasmid; possible unintended gene insertion products produced by a single cross-over of the recircularized plasmid are shown in FIG. 1C.

Example 2

Initial Gene Replacement Procedures

Initial methods of targeting of the DG17 locus employed plasmid 17Nt, linearized at an XmnI site within the vector.

Figure 2:
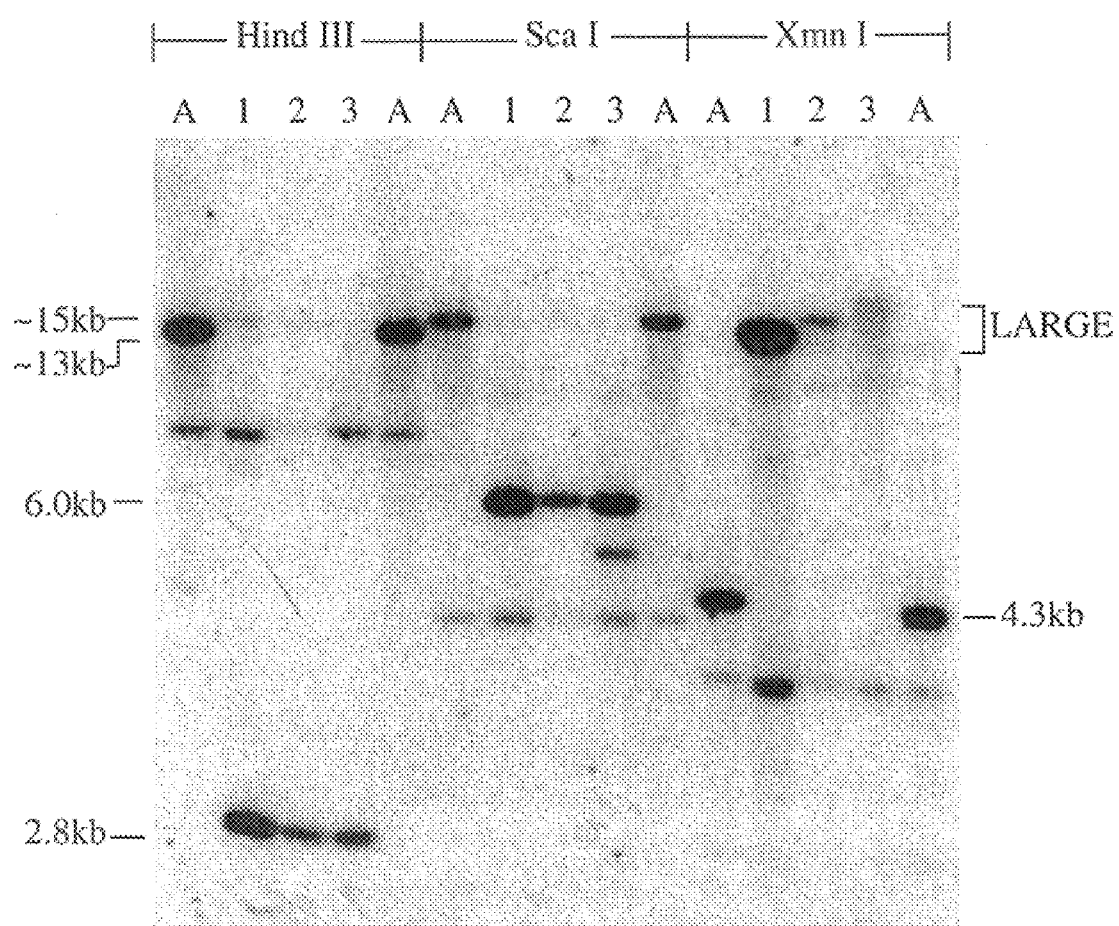
FIG. 2 shows the results of the DG17 locus targeted with untreated DNA. DNA from parental AX2 cells (lanes A) and from three clones transformed with XmnI-linearized 17Nt plasmid DNA (clones 1,2, and 3) was digested with the restriction enzyme indicated, and subjected to gel electrophoresis using a 0.6% agarose gel. The gel was blotted and the blot probed with a radio-labeled 300 bp BglII-HindIII restriction fragment of the adjacent gene, CP1 (Williams, J. G. et al. (1985) EMBO J. 4, 999–1006).

Methods of distinguishing between targeted and non-targeted recombination events included screening G418-resistant transfected clones by PCR (Kim, H.-S. et al. (1988) Nucleic Acids Res. 16, 8887–8903), using a neo gene primer (SEQ ID NO: 1) and a second primer specific to the CP1 gene (SEQ ID NO: 2) immediately adjacent to the DG17 chromosomal locus. Putative targeted, PCR-positive cells were repurified on plates containing solid medium, then propagated in liquid medium. DNA from each clone of cells was extracted, digested, and analyzed by Southern blot (FIG. 2). The probe chosen was the BglII-HindIII restriction fragment of the neighboring gene, CP1 (Williams et al. (1985) EMBO J. 4, 999–1006).

As shown in FIG. 2, the hybridizing restriction fragments of the parental AX2 strain (roughly 13 kb in the HindIII digest, 15 kb in the ScaI digest, and 4.3 kb in the XmnI digest) were altered in each of three transfectant clones, verifying that there was homologous targeting in each clone. Fainter bands (8 kb, HindIII; 4.3 kb, ScaI; 3.7 kb, XmnI) can have been the result of cross-hybridization of this CP1 probe which includes part of the conserved active site) to the closely related protease CP2 (contrast FIG. 4C, which uses SEQ ID Nos: 9 and 10 as probes). The newly generated HindIII band (2.8 kb) was determined to be of predicted size for the intended double cross-over event (cf. FIG. 1b); but the new ScaI band (6.0 kb) and XmnI bands (variable in size, but all large) were not. (Double-crossover products of about 17 kb [ScaI] and 10 kb [XmnI] were predicted.) Further, the observed sizes of HindIII and ScaI bands could have arisen by homologous recombination involving a recircularized plasmid (or plasmids) insertionally targeting the 5' region of DG17 homology (FIG. 1C). The sizes of the large and variable XmnI fragments could have been obtained by 5' insertion of one or more plasmid molecules, assuming that the XmnI site was not restored by recircularization, as DNA ends are sufficiently altered during transformation to eliminate a restriction site (Goedecke, W. et al. (1994) Nucleic Acids Res. 22, 2094–2101).

The data from these clones show that transforming DNA successfully targeted the DG17 locus however the sizes of the inserts indicate that a recombination event other than the intended double cross-over replacement event had occurred.

Example 3

Blocking the Ends of Transforming DNA

Events such as recircularization of linearized plasmids, joining of such linear molecules to form multi-copy arrays, and integration of whole linear plasmids into the host's genome involve ligation of the ends of transforming DNA molecules. In contrast, homologous double-crossover integration, being an event involving internal portions of the DNA molecule, does not involve the ends.

Figure 3:
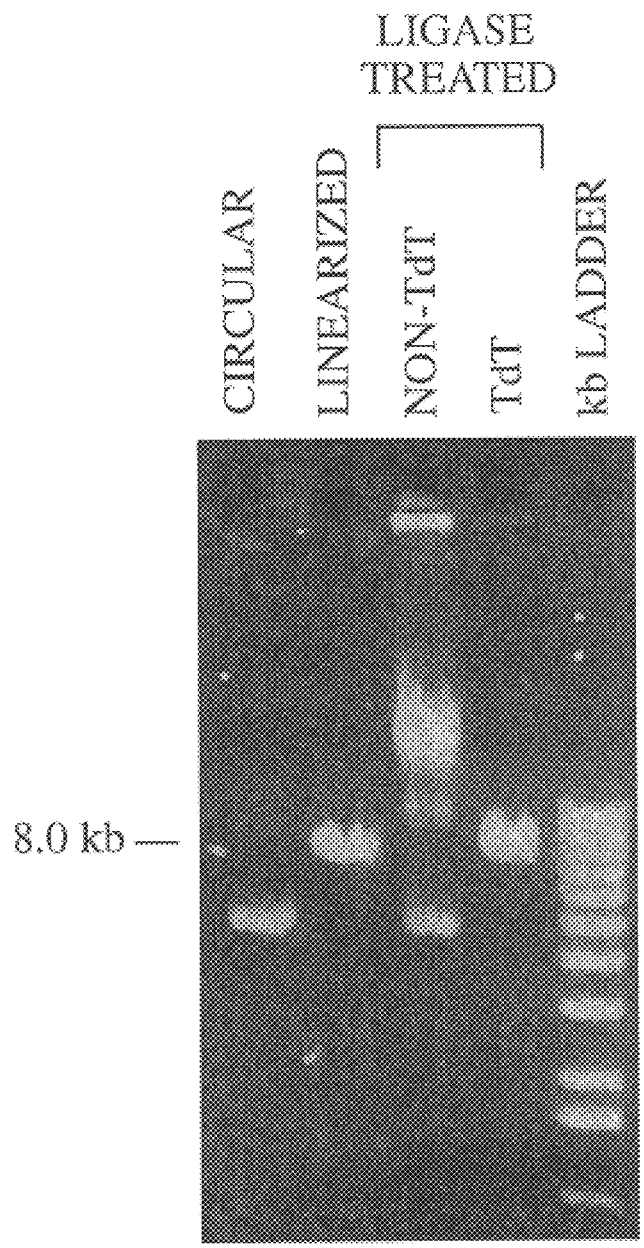
FIG. 3 shows blocking of DNA termini by treatment with terminal dideoxynucleotidyl transferase (TdT) and 2'3' dideoxyATP. 17Nt plasmid DNA was linearized by digestion with AlwNI (which produces 3' protruding termini, the preferred substrate for TdT treatment), its ends modified by treatment with TdT and 2'3' dideoxyATP, and finally incubated with DNA ligase. Control DNA was AlwNI-linearized and re-ligated in the absence of TdT treatment. Circular plasmid DNA, linearized DNA, and all ligation products were analyzed by electrophoresis on a 0.5% agarose gel containingethidium bromide, and the gel was photographed under UV illumination. Ligation of untreated linear DNA resulted in production of circular and/or multimeric molecules. The presence of 2'3' dideoxy modification of DNA ends completely inhibited ligation.

In order to prevent DNA ligation of plasmid molecules, the ends of transfecting DNA were blocked in a manner which amoebae presumably do not naturally encounter, namely with a 2'3' dideoxynucleotide. FIG. 3 shows the results of an in vitro test of the blocking procedure. It was observed that the addition to linear plasmid DNA of 2'3' dideoxy AMP (dideoxyAMP) by the enzyme terminal deoxynucleotidyl transferase (TdT) effectively prevents T4 DNA ligase from joining treated molecules into circular, dimeric, or oligomeric forms. Linearized 2'3' dideoxy-blocked plasmid was used to transfect Dictyostelium amoebae, to determine whether cells are incapable of excising and/or ligating blocked 3' ends also fail to achieve recircularization of the plasmid.

Example 4

Gene Replacement Using Transforming DNA With 2'3' Dideoxy-blocked Ends

FIG. 4 presents an analysis by Southern blotting of DG17 locus DNA extracted from a dozen independent 17Nt transformants. Plasmid DNA was linearized for transformation with AlwNI (clones T1–T5 and 1–3) or XmnI (clones 4–7) as identified in FIG. 4. The concentration of G418 used was: 15 µg/ml for clones T3–T5, 1–3 and 7; and 6,10, and 20 µg/ml respectively for clones T1, T2, and 4–6. Untreated clones 5 and 6 shown in FIG. 4 are the same as transformants 2 and 3 of FIG. 2. For PCR screening of transformants for DG17, cell lysates were treated with proteinase K prior to amplification. Hybridization probes were synthesized by asymmetric PCR; the CP1 probe (SEQ ID NOs: 9 and 10) used here differs from that of FIG. 2 and was chosen to minimize cross-hybridization with CP2. In between probings, the blot was stripped of hybridizing DNA by twice pouring boiling 0.5% SDS over the membrane and allowing it to cool to room temperature. The middle lanes of the figure compare six clones obtained from a single round of transformation, in which half of the transformants (T3–T5) were obtained from cells transformed with TdT-treated DNA, and half (1–3) were obtained from cells transformed with linearized but otherwise untreated DNA. Additional clones obtained from several other experiments testing the effects of TdT treatment are also shown in FIG. 4: clones T1 and T2 were derived from cells receiving TdT-treated DNA, and clones 4–7 were derived from cells receiving untreated DNA.

Figure 4A:
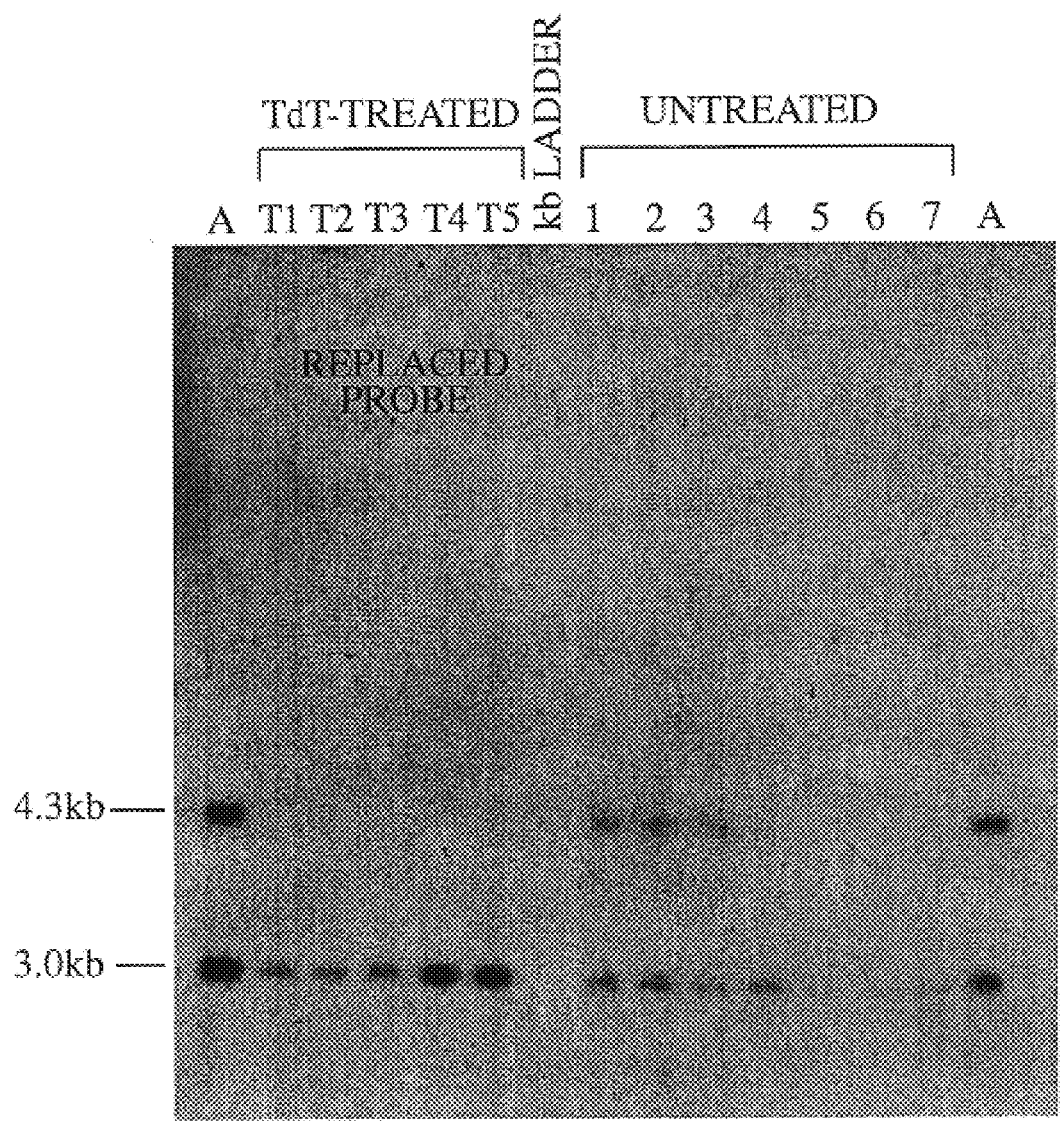
FIGS. 4A–4D shows the results of gene targeting with 2'3' dideoxy-blocked DNA. DNA was extracted from cells of the parental line AX2 (lanes A), and from 12 transformants. DNA was digested with XmnI, and subjected to gel electrophoresis (0.6% agarose), blotting, and hybridization with the probe indicated in each panel. Samples T1–T5 were derived from clones transformed with 2'3' dideoxy-treated DNA; samples 1–7, from linearized but otherwise untreated plasmid DNA. The region of DNA corresponding to each probe is indicated in FIG. 1. Clones T1 and T2 (blocked ends) and 4–7 (control untreated ends) represent clones obtained previously and at different times; clones T3–T5 and 1–3 were obtained from a single experiment in which half the DNA was 2'3' dideoxy-blocked and half untreated, respectively.
Figure 4B:
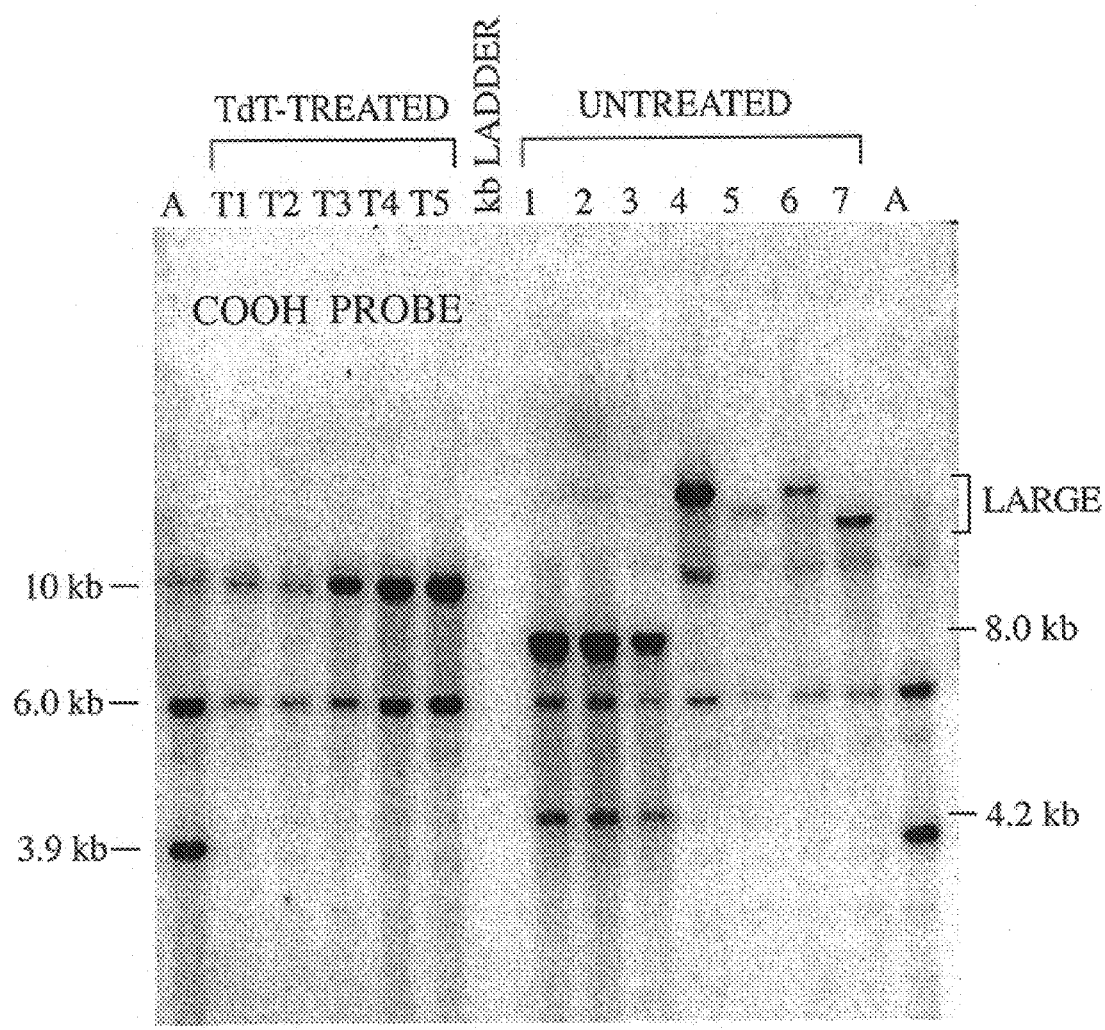
Figure 4C:
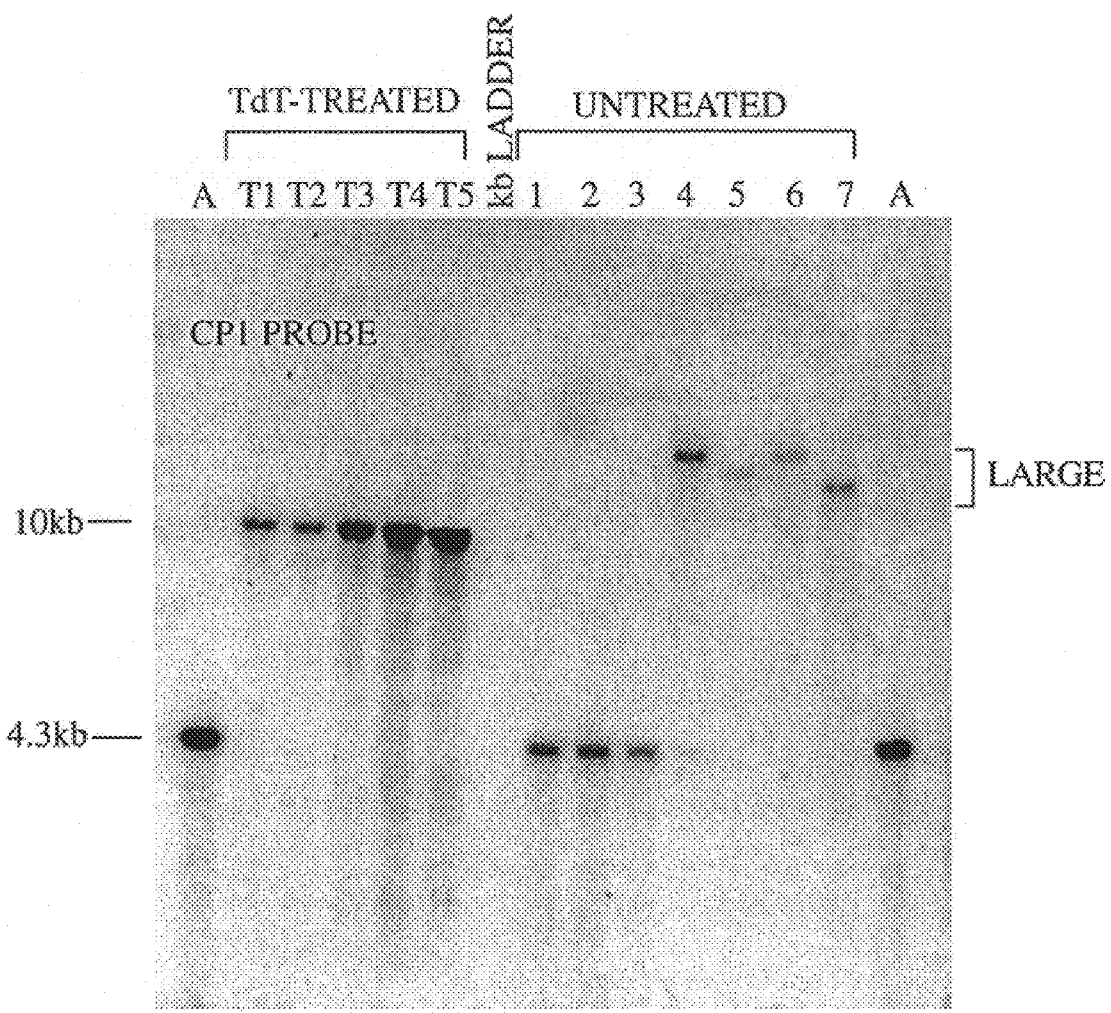
Figure 4D:
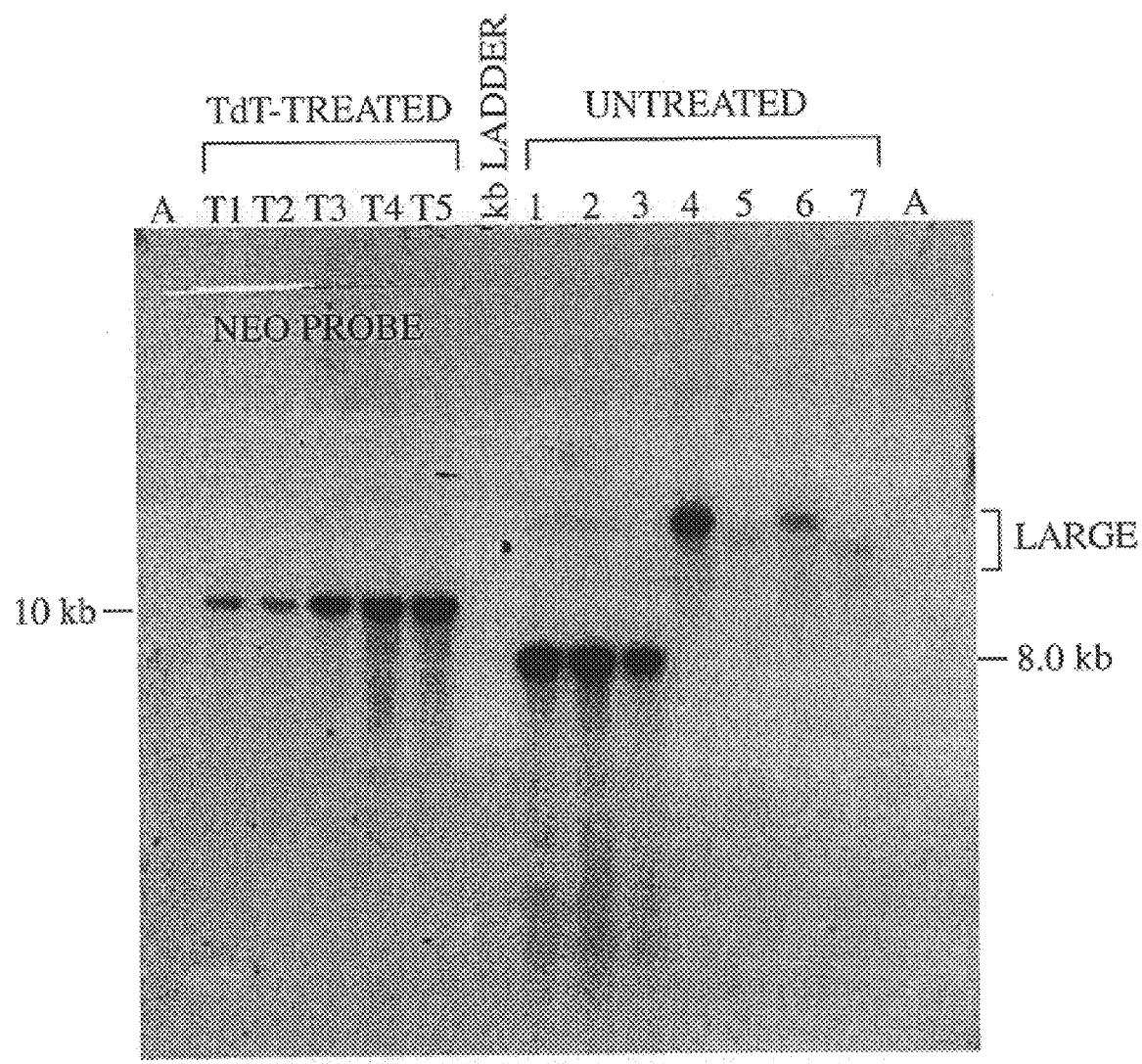

The two parental strain AX2 DNA samples (A, the left- and right-most lanes) showed that the Dictyostelium genome contains, in addition to gene DG17, a closely related gene which cross-hybridized strongly to all DG17 structural gene probes. The probe that identifies the central EcoRI fragment of DG17 (the "Replaced region probe"; SEQ ID NOs: 3 and 4) used in FIG. 4A hybridizes to the DG17 locus itself (on a 4.3 kb XmnI fragment) and the related gene (3.0 kb). The two loci were visualized also with a probe that identifies the carboxy-terminal portion of the coding region ("COOH probe"; SEQ ID NOs: 7 and 8) as shown in FIG. 4B: DG17 appeared as a 3.9 kb band and the related gene as a 6.0 kb band. The DG17 locus fragment uniquely hybridized to the adjoining CP1 probe (the 4.3 kb band is seen again in FIG. 4C). Neither locus of strain AX2 was seen when the blot was probed with "Neo" (heterologous; SEQ ID NOs: 5 and 6) DNA (FIG. 4D).

The data show that the five clones (T1–T5) obtained from transformation with 2'3' dideoxy-blocked DNA resulted from homologous double-crossover gene replacement events. The replaced region probe did not bind to the disrupted DG17 locus in the DNA of these clones. This probe did anneal to the unaffected related gene (FIG. 4A). The targeted DG17 locus of these clones was observed to be located on a single 10.0 kb XmnI fragment, which was detected by each of the COOH, CP1, and Neo probes. The replacement,event eliminated the central XmnI site of the wild type DG17 locus. The hybridization of only this 10.0 kb XmnI DNA fragment to both the Neo and CP1 probes demonstrated that no additional copies of the selected neomycin resistance gene were observed in any of these cells, either at the targeted locus or randomly integrated into other loci. These data show that the clones were generated as a result of the desired double-crossover recombination path (FIG. 1B).

Data obtained from clones transformed with untreated DNA ends (clones 1–7) showed that targeted DG17 loci which result were variable in structure. The central EcoRI fragment of the gene persisted in clones 1–3, but was excised in clones 4–7, as determined by hybridization with the replaced region probe of FIG. 4A. Thus, targeting included a gene replacement event in clones 4–7, but not in 1–3. Probing clones 1–3 with CP1 DNA (FIG. 4C) shows the 5' side of the DG17 locus to be intact. However, these same clones generated altered DG17 locus restriction fragments when tested with the COOH probe: the 4.2 kb bands in FIG. 4B were reproducibly larger than those of AX2, and a band of 7.5 kb (somewhat obscured in this exposure by the intense hybridization at 8 kb) was generated. These clones may have arisen via an insertional recombination event within the region of vector/chromosome homology at the 3' end of DG17, as indicated by data obtained from probing ScaI digested DNA. The clones were found to contain, in addition, multiple copies of intact targeting DNA, as is evident in the prominent band of 8.0 kb detected by the both the COOH and Neo probes in FIGS. 4B and 4D (and confirmed by ScaI restriction digestion). This band presumably represents multi-copy, tandem vector arrays integrated into the genome either at the DG17 locus or elsewhere.

Analysis of DNA from the four clones created by untreated DNA which have undergone gene replacement (4–7, FIG. 4A) also revealed complex patterns. The 5'probe (FIG. 4B) hybridized to large, variably-sized XmnI fragments in each of the four transformants, and these fragments were detected also by the COOH and Neo probe:; (FIGS. 4C and 4D). These bands were not generated by a simple double-crossover gene replacement event. CP1 probing of ScaI-digested DNA of two of these clones (FIG. 2) is consistent with a complex 5' insertion event. The data indicate that a combination of a double-crossover event and a 5' insertion event occurred in these cells. Thus, none of the clones resulting from transformation with untreated linear DNA targeted the DG17 locus precisely, in contrast to the uniform successful gene replacement events obtained by transformation using DNA with blocked 3' ends.

Example 5

The Role of the Lethal UAA-suppressing tRNA Gene

To examine the role of the lethal (counterselectable) tRNA gene, DG17-targeted clones obtained by transformation with a vector similar to 17Nt but lacking the tRNA gene, were prepared. Negative selection using tRNA showed that the tRNA alone did not give clean, double-crossover gene replacement targeting (Morrison, A. et al.(1997) Gene 202, 171–176, and FIGS. 2 and 4). The presence of dideoxyAMP at 3' termini may partially protect the ends of the DNA encoding TRNA against limited exonucleolytic degradation thereby enhancing negative selection. Alternatively, the silencing of expression of transgenes in tandem repeats (Dorer, D. R. et al. (1994) Cell 77, 993–1002) may allow for the persistence of the suppressor tRNA gene in transformants derived from untreated DNA. Retention of an ostensibly lethal, counter-selecting gene in random integrants has been observed with mammalian cells (Mansour, S. L. et al. (1988) Nature 336, 348–352; Horie, K. et al. (1994) J. Biochem. 115, 477–485).

To determine if the 2'3' dideoxy blockage of DNA ends might prevent unwanted DNA insertion even in the absence of the suppressor tRNA, blots of such clones were prepared and analyzed. These blots revealed a variety of complex targeting events including the insertion of multiple copies of the selected neo gene. These data indicate that the cells can remove the blocking 2'3' dideoxynucleotide to some extent, enabling these ends to participate in DNA repair and ligation. The data further show that to achieve a clean double-crossover gene replacement of the DG17 locus, transforming DNA required both the counter-selecting tRNA gene and 2'3' dideoxy modification of its ends.

Example 6

Copy Number From G418 Selection of neo Transformants

G418 selection of Dictyostelium transformants is widely used, and most clones obtained by this selection contain several if not many copies of the selected neo vector (Knecht, D. A. et al. (1986) Mol. Cell. Biol. 6, 3973–3983). In contrast, the clones obtained herein contained a single, targeted copy of the neo gene. Thus, single-copy G418-resistant transformants, avoiding the introduction of multiple copies of neo and whatever gene is selected for targeting by the methods herein, can be obtained by the use of relatively low concentrations of G418, tRNA counter-selection, and especially 3' end modification.

Example 7

Thymidine Kinase Selection in Mammalian Cells

The G418/tRNA "positive/negative" vector selection here can be adapted for the targeting of mammalian genes using G418/thymidine kinase (TK) vectors. The TK gene (causing sensitivity to gancyclovir) has been used to attempt to eliminate non-homologous integration and result in precise gene replacement. However, it is observed that a considerable background of non-targeted clones persists (Mansour, S. L. et al. (1988) Nature 336, 348–352; Horie, K. et al. (1994) J. Biochem. 115, 477–485). Additionally, some of the targeted clones might suffer unanticipated, insertion-type events at the same locus. Undesired mammalian gene targeting products, involving DNA end-mediated reactions, can be avoided or reduced by combining TK counter-selection with an embodiment of the present invention, i.e., a method for 2'3' dideoxynucleotide modification of transforming DNA. (Similar complex events have been observed in Drosophila gene targeting; see Cherbas, L. et al (1997) Genetics 145, 349–358.)

Example 8

Inactivation of a Target Gene

To create an animal model system for the study of a human disease, the compositions and methods of the dideoxy system herein can be used to target a gene in the genome of a cell, for example in an embryonic cell which can then be placed in the blastocyst of a female animal in a very early stage of pregnancy. The animal can be, for example, a rodent such as a mouse or rat, or a dog, a pig, a sheep, a cow, or a monkey or a higher ape. Examples of genes to target to provide useful animal models using various embodiments of the invention include genes selected from the group which in an inactivated state cause diseases such as cystic fibrosis, Lesch-Nyhan syndrome, breast cancer, emphysema, and muscular dystrophy.

Further, the technology can be used to eliminate an antigen, for example, an antigen encoded by a gene in the genome of a pig that would otherwise limit use of a pig organ or tissue as a source for heterologous transpecies transplantation, or xenograft.

The technology can be used to inactivate a gene in a plant, for example a gene encoding an antigen, or an enzyme involved in synthesis of an antigen, which antigen is an allergan for a human population. Examples are an antigen encoded by a gene in a peanut plant, Arachis hypogaea, or in plant which produces a Brazil nut, Bertholletia excelsa.

Example 9

Gene Replacement in Human Disease

Gene replacement is suitable for therapy of monogenic diseases which are recessive, such as adenosine deaminase deficiency (ADA), resulting in SCID (severe combined immuno-deficiency), cystic fibrosis, (CF), Duchenne muscular dystrophy (DMD), phenylketonuria (PKU), sickle cell anemia, α-thalassemia, β-thalassemia, breast cancer, and Crigler-Najjar syndrome.

Suitable dominant autosomal disorders for which a properly targeted event should be curative and which are detectable by pre-natal diagnosis include: achondroplasia, Marfan syndrome, neurofibromatosis, myotonic dystrophy and Huntington disease (HD).

Gene replacement can be performed for a gene that is chromosomal or that is extra-chromosomal, for example, a mitochondrial gene.

Example 10

Gene Replacement in a Plant

A DNA sequence encoding a novel allele can be inserted into the genome of a plant, for example, into a gene that is located on a chromosome, or in a self-replicating plastid such as a chloroplast or a chromoplast, or in a mitochondrion of a plant cell. A gene sequence which is located in a plastid such as a chloroplast does not contribute substantially to the genome of a haploid pollen cell, or the contribution is greatly reduced compared to that of a nuclear gene sequence which is located on a chromosome. A recombinant food crop plant can be contained in the field to a greater extent if the sequence does not contribute to pollen, which can be distributed over a wide geographic area by wind or by insect dispersion.

What is claimed is:

1. A method of replacing a target sequence in a chromosomal gene of a eukaryotic cell, comprising: providing a replacement sequence on a linearized gene-targeting plasmid having ends that are modified to contain a terminating nucleotide analog, the analog preventing the ends of the linearized plasmid from being ligated, so that the target sequence in the chromosomal gene is replaced by the replacement sequence and unintended DNA insertion is inhibited.

2. A method according to claim 1, wherein the replacement sequence is flanked by sequences that are substantially homologous to non-identical portions of the target gene, the method further comprising: transforming the cell with the targeting plasmid so that a precise double crossover recombination event occurs between each of the non-identical portions of the target gene and the substantially homologous sequences on the plasmid.

3. A method according to claim 2, wherein the recombination event causes inactivation of a function of the target gene.

4. A method according to any of claims 1–3, wherein the terminating nucleotide analog is a 2',3'-dideoxynucleotide.

5. A method according any of claims 1–3, wherein the replacement sequence further encodes a selectable phenotype.

6. A method according to claim 5, wherein the selectable phenotype is resistance to a drug.

7. A method according to claim 6, wherein the selectable phenotype is resistance to G418.

8. A method according to claim 4, wherein the terminating 2',3'-dideoxynucleotide analog is selected from the group consisting of 2',3'-dideoxyadenosine monophosphate, 2'3'-dideoxythymridine monophosphate, 2',3'-dideoxycytidine monophosphate, and 2',3'-dideoxyguanosine monophosphate.

9. A method according to claim 8, wherein adding the 2',3'-dideoxynucleotide to the modified ends of the linearized plasmid is performed with an enzyme selected from the group consisting of a terminal deoxynucleotidyl transferase and a DNA polymerase.

* * * * *

UNITED STATES PATENT AND TRADEMARK OFFICE
CERTIFICATE OF CORRECTION

PATENT NO. : 6,498,036 B1 Page 1 of 1
DATED : December 24, 2002
INVENTOR(S) : Ratner It is certified that error appears in the above-identified patent and that said Letters Patent is hereby corrected as shown below:

Column 13,
Line 56, delete "and unintended DNA insertion is inhibited"

Column 14,
Line 60, delete "dideoxythymridine" and insert -- dideoxythymidine --.

Signed and Sealed this

Second Day of December, 2003

JAMES E. ROGAN
*Director of the United States Patent and Trademark Office*

SEQUENCE LISTING

<160> NUMBER OF SEQ ID NOS: 10

<210> SEQ ID NO 1
<211> LENGTH: 39
<212> TYPE: DNA
<213> ORGANISM: PCR Primer

<400> SEQUENCE: 1
tgggttttaa aattttcaaa taaataatta accaaccca                                  39

<210> SEQ ID NO 2
<211> LENGTH: 28
<212> TYPE: DNA
<213> ORGANISM: PCR Primer

<400> SEQUENCE: 2
gatcctaata gaaccccat tccttttt                                              28

<210> SEQ ID NO 3
<211> LENGTH: 35
<212> TYPE: DNA
<213> ORGANISM: PCR Primer

<400> SEQUENCE: 3
catctggtgg tgaacaattt gttccacctt caacg                                     35

<210> SEQ ID NO 4
<211> LENGTH: 35
<212> TYPE: DNA
<213> ORGANISM: PCR Primer

<400> SEQUENCE: 4
aatgatttat caagatgttt gatggtagag cgtgc                                     35

<210> SEQ ID NO 5
<211> LENGTH: 24
<212> TYPE: DNA
<213> ORGANISM: PCR Primer

-continued

```
<400> SEQUENCE: 5
atggtcagac taaactggct gacg                                              24

<210> SEQ ID NO 6
<211> LENGTH: 24
<212> TYPE: DNA
<213> ORGANISM: PCR Primer

<400> SEQUENCE: 6
ttccagactt gttcaacagg ccag                                              24

<210> SEQ ID NO 7
<211> LENGTH: 31
<212> TYPE: DNA
<213> ORGANISM: PCR Primer

<400> SEQUENCE: 7
caaaagttca tcatgagttt tctttgattg g                                      31

<210> SEQ ID NO 8
<211> LENGTH: 32
<212> TYPE: DNA
<213> ORGANISM: PCR Primer

<400> SEQUENCE: 8
gctcacaagg ttgttcagtg aaaattgaaa gg                                     32

<210> SEQ ID NO 9
<211> LENGTH: 25
<212> TYPE: DNA
<213> ORGANISM: PCR Primer

<400> SEQUENCE: 9
catgaagaat atttggaaag atttg                                             25

<210> SEQ ID NO 10
<211> LENGTH: 23
<212> TYPE: DNA
<213> ORGANISM: PCR Primer

<400> SEQUENCE: 10
caagataatc agcaactgga agg                                               23
```